United States Patent [19]
Lind

[11] Patent Number: 5,820,630
[45] Date of Patent: Oct. 13, 1998

[54] MEDICAL FORCEPS JAW ASSEMBLY

[75] Inventor: Stuart J. Lind, Edina, Minn.

[73] Assignee: Annex Medical, Inc., Eden Prairie, Minn.

[21] Appl. No.: 735,239

[22] Filed: Oct. 22, 1996

[51] Int. Cl.⁶ .................................................. A61B 17/28
[52] U.S. Cl. ......................... 606/208; 606/205; 128/751
[58] Field of Search ..................... 128/751, 752; 606/205, 206, 208, 142, 119; 604/22; 600/221; 81/416

[56] References Cited

U.S. PATENT DOCUMENTS

| | | | |
|---|---|---|---|
| 4,522,206 | 6/1985 | Whipple et al. | 128/752 X |
| 4,721,116 | 1/1988 | Schintgen et al. | 128/751 |
| 4,785,825 | 11/1988 | Romaniuk et al. | 128/751 |
| 4,881,550 | 11/1989 | Kothe | 128/752 |
| 4,887,612 | 12/1989 | Esser et al. | 128/751 |
| 5,052,402 | 10/1991 | Bencini et al. | 128/751 |
| 5,082,000 | 1/1992 | Picha et al. | 128/751 |
| 5,133,727 | 7/1992 | Bales et al. | 606/170 |
| 5,156,608 | 10/1992 | Troidl et al. | 606/642 |
| 5,156,609 | 10/1992 | Nakao et al. | 606/205 X |
| 5,172,700 | 12/1992 | Bencini et al. | 128/751 |
| 5,228,451 | 7/1993 | Bales et al. | 128/751 |
| 5,238,002 | 8/1993 | Devlin | 128/751 |
| 5,281,230 | 1/1994 | Heidmueller | 606/205 X |
| 5,318,589 | 6/1994 | Lichtman | 128/751 X |
| 5,325,866 | 7/1994 | Krzyzanowski | 128/751 |
| 5,373,854 | 12/1994 | Kolozsi | 128/749 |
| 5,394,885 | 3/1995 | Francese | 128/751 |
| 5,471,992 | 12/1995 | Banik et al. | 128/751 |
| 5,482,054 | 1/1996 | Slater et al. | 128/751 |
| 5,535,754 | 7/1996 | Dorerty | 128/751 |

*Primary Examiner*—Michael H. Thaler

[57] ABSTRACT

A medical forceps jaw assembly for obtaining biopsy specimens or grasping objects. The forceps has a jaw assembly which incorporates a clevis pivot. The clevis pivot has a cross hole which is parallel to the center line of the jaw assembly. This cross hole, along with the lumens of the clevis and the shaft comprise a passageway. A diagnostic or procedural member can be passed through this passageway. By incorporating the diagnostic or procedural member into the passageway of the medical forceps, the need for two separate devices is eliminated for procedures which require both. By locating the cross hole appropriately in the clevis pivot, the diagnostic or procedural member can be centered between the two jaws. When used with an endoscope, the device allows two functions to be simultaneously accomplished using an endoscope with only one working channel. The design of the device is simple and cost effective.

20 Claims, 1 Drawing Sheet

MEDICAL FORCEPS JAW ASSEMBLY

BACKGROUND-FIELD OF INVENTION

This invention relates to biopsy forceps, specifically to such forceps which incorporate a passageway for diagnostic or procedural instrumentation.

BACKGROUND-DESCRIPTION OF PRIOR ART

When making an endoscopic examination of tissue in a particular site in a patient's body, it is common for the physician to take a tissue sample from that site for analysis. A number of different types of biopsy forceps for taking a small tissue sample are in use. Typically, such biopsy forceps consist of a small diameter flexible shaft which can be passed through the lumen of an endoscope. Attached to the distal end of this shaft is a pair of sharp jaws which can be opened and closed to cut and hold a small tissue sample for analysis. The opening and closing of the jaws is controlled manually by manipulating controls located at the proximal end of the shaft. One design of the jaw assembly incorporates a clevis pivot about which the two jaws rotate. Another design is for the two jaws to be hinged at their proximal end. The clevis pivot design allows the jaws to be closed with a greater closing force than designs which incorporate a hinge.

One example of a biopsy forceps which incorporates a hinge may be seen with reference to U.S. Pat. No. 5,172,700 to Bencini et al. Examples of biopsy forceps which incorporate a clevis pivot may be seen with reference to U.S. Pat. No. 4,721,116 to Schintgen et al., U.S. Pat. No. 4,887,612 to Esser et al., U.S. Pat. No. 5,133,727 to Bales et al., U.S. Pat. No. 5,228,451 to Bales et al., U.S. Pat. No. 5,238,002 to Devlin et al., and U.S. Pat. No. 5,325,866 to Krzyzanowski. None of the above referenced patents disclose a device for which a passageway exists which would allow passage of diagnostic or procedural instrumentation through the shaft and jaw assembly of the device.

Biopsy forceps which incorporate a hinge design have been made which will allow passage of diagnostic or procedural instrumentation through the shaft and jaw assembly of the device. Examples can be seen with reference to U.S. Pat. No. 5,373,854 to Kolozsi, and U.S. Pat. No. 5,471,992 to Banik et al. However, the hinged design of these devices results in less jaw closing force than devices which have a clevis pivot design.

For certain procedures, it may be necessary or desirable for the physician to use a second device in conjunction with the biopsy forceps for diagnostic or procedural purposes. With the prior art biopsy forceps which incorporate a clevis pivot, this requires an endoscope which has two working channels: one for the biopsy forceps and one for the second diagnostic or procedural device. An endoscope with two working channels has the disadvantage of having greater shaft diameter, which may inhibit its passage into narrow body channels. Additionally, the need to use an endoscope with two working channels for some procedures may require the physician to have available both one and two channel endoscopes.

It may also be desirable for the diagnostic or procedural device to actually pass through the biopsy forceps. Examples of this feature are a guidewire over which the biopsy forceps is placed to help guide the forceps to the proper location, or a device which could be used to verify the presence and size of the biopsy sample after it is secured in the jaws. With the prior art biopsy forceps which incorporate a clevis pivot, this would not be possible.

OBJECTS AND ADVANTAGES

Accordingly, several objects and advantages of the present invention are:

(a) to provide a novel biopsy forceps which incorporates a passageway for extending diagnostic or procedural instrumentation through the shaft and jaw assembly of the device, thus making the simultaneous use of two devices through an endoscope with only one working channel possible;

(b) to provide a novel biopsy forceps of the type described herein which uses a mechanism, such as a clevis pivot, which provides the jaws of the forceps with the greatest possible force for closing the jaws, thus providing effective sample retrieval.

(c) to provide a novel biopsy forceps of the type described herein, for which the diagnostic or procedural instrumentation can be centered between the jaws;

(d) to provide a novel biopsy forceps of the type described herein, for which diagnostic or procedural instrumentation can be incorporated into the device, thus eliminating the need for a second, separate device;

Further objects and advantages are to provide a biopsy forceps of the type described herein which is of simple design, is simple and inexpensive to manufacture, and is easy to use. Still further objects and advantages will become apparent from a consideration of the ensuing description and drawings.

REFERENCE NUMERALS IN DRAWINGS

| | |
|---|---|
| 8 jaw assembly | 28 pull wires |
| 10 clevis pivol | 30 coil |
| 12 cross hole | 32 slot |
| 14 flare | 34 angled bends |
| 16 elongated diagnostic or procedural member | 36 notch |
| 18 cup | 38 shaft |
| 20 sharp rim | 40 engagement hole |
| 22 jaw | 42 clevis arm |
| 24 passageway | 44 clevis arm hole |
| 26 clevis | 46 jaw pivot hole |

Description-FIGS. 1 to 4

Figure 1:
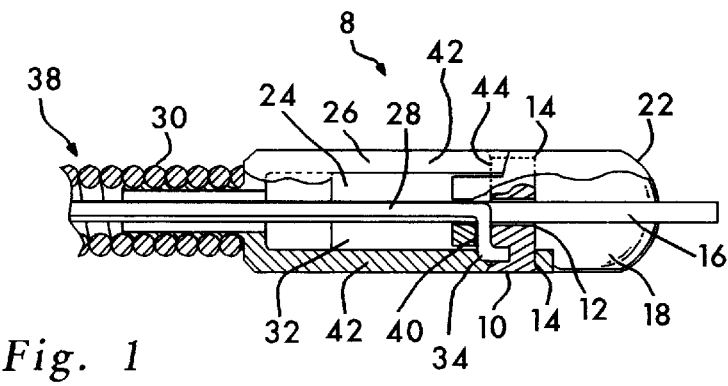
FIG. 1 is a plan view, partly in section, of the jaw assembly with its jaws in the open position.
Figure 2:
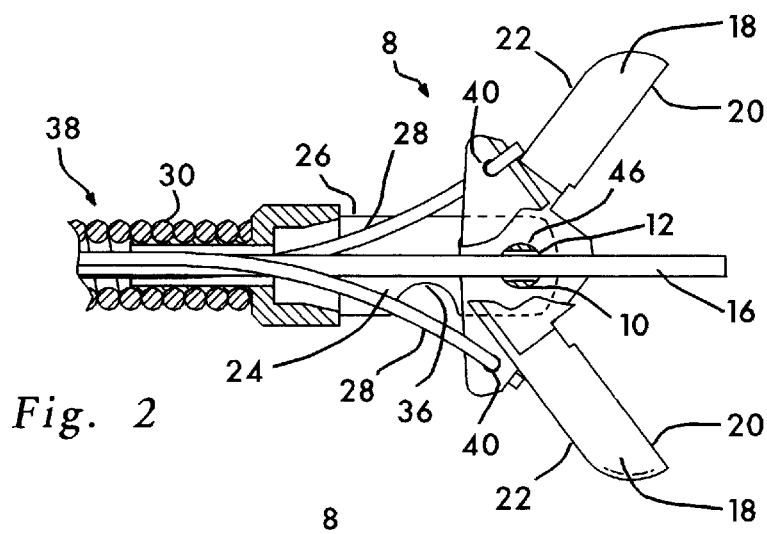
FIG. 2 is a side elevational view, partly in section, of the jaw assembly shown in FIG. 1 with its jaws in the open position.
Figure 3:
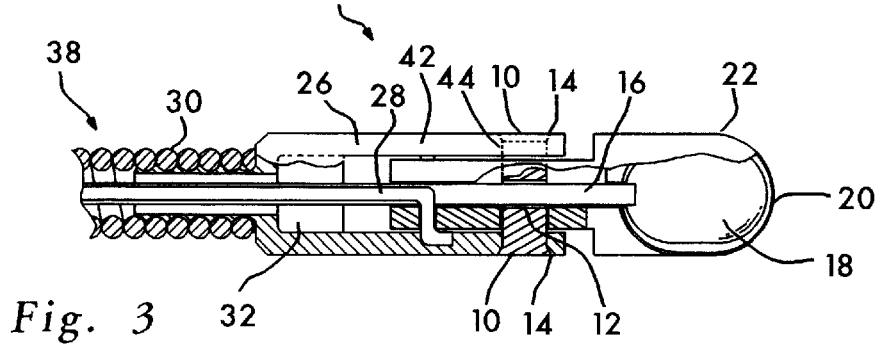
FIG. 3 is a plan view, partly in section, of the jaw assembly with its jaws in the closed position.
Figure 4:
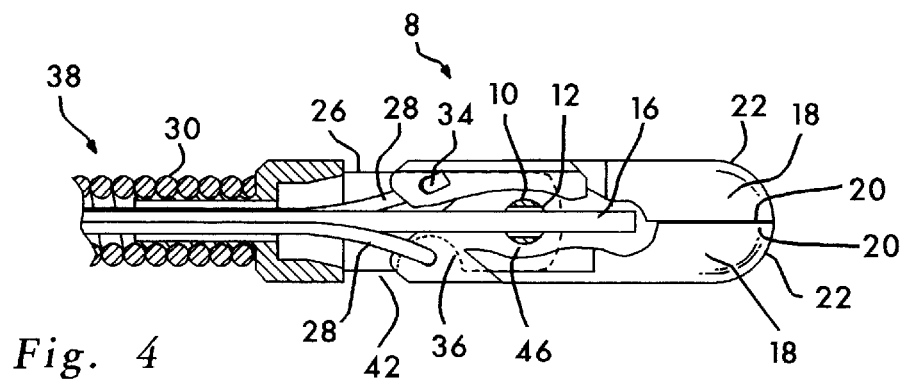
FIG. 4 is a side elevational view, partly in section, of the jaw assembly shown in FIG. 3 with its jaws in the closed position.

A typical embodiment of the biopsy forceps jaw assembly of the current invention is illustrated in FIGS. 1 and 3 (top view) and FIGS. 2 and 4 (side view). The biopsy forceps has a shaft 38, constructed of a steel coil 30, polymeric tubing, or other flexible material which has a lumen through its entire length. A suitable control mechanism (not shown) is located at the proximal end of shaft 38, from which the control of the device is effected by the user. A jaw assembly 8 is located at the distal end of shaft 38, and consists of a clevis 26, two jaws 22, and a clevis pivot 10. The proximal end of clevis 26 is attached to the distal end of shaft 38. Clevis 26 may be threaded, allowing it to be screwed into coil 30, which may comprise shaft 38, or clevis 26 may be attached to shaft 38 by other similar means. Clevis 26 has two clevis arms 42 which are located at the distal of clevis 26. Between clevis arms 42 is a slot 32. Clevis 26 has a lumen extending from its proximal end to slot 32. Located near the distal end of each clevis arm 42 is a clevis arm hole 44. Jaws 22 each have a jaw pivot hole 46. The proximal ends of both jaws 22 are located in slot 32. Jaws 22 are attached to clevis 26 by means of clevis pivot 10, which passes through each of the two jaw pivot holes 46 and each of the two clevis arm holes 44. Clevis pivot 10 has a flare 14 at each end, securing it and jaws 22, in place. Each jaw 22 has a cup 18 located at its distal end. The open portions of the two cups 18 face each other. Each cup 18 has a sharp rim 20, which at minimum is located on the distal portion of each cup 18, and may extend completely around the edge of each cup 18. Referring to FIG. 4, which shows jaws 22 in the closed position, sharp rims 20 of the two cups 18 are aligned so as to meet. The two cups 18 thus form a closed space between them.

The control mechanism (not shown) is connected to the proximal ends of a pair of pull wires 28, which pass through shaft 38 and the proximal portion of clevis 26. Pull wires 28 do not fill the lumen of shaft 38 nor the proximal end of clevis 26. The distal end of one of the pull wires 28 passes through an engagement hole 40 located near the proximal end of one jaw 22. Similarly, the distal end of the other pull wire 28 passes through an engagement hole 40 located near the proximal end of the other jaw 22. At the distal end of each pull wire 28 are located two angled bends 34. For each of the two pull wires 28, one of the angled bends 34 is located on each side of respective engagement hole 40, attaching each pull wire 28 to its respective jaw 22. A notch 36 is located on each clevis arm 44. Clevis pivot 10 has an opening, or cross hole 12, through it, parallel to shaft 38. Thus a passageway 24 exists which extends from the distal portion of clevis pivot 10 proximally through clevis 26 and shaft 38. An elongated diagnostic or procedural member 16 can be passed through shaft 38, clevis 26, and cross hole 12. In one embodiment of the biopsy forceps, elongated diagnostic or procedural member 16 is a separate device. In another embodiment, elongated diagnostic or procedural member 16 is a component of the biopsy forceps.

From the description above, a number of advantages of my biopsy forceps become evident:

(a) A diagnostic or procedural member can be passed through the shaft and jaw assembly of the biopsy forceps and into the jaw area. This eliminates the need to for a two channel endoscope when certain diagnostic or procedural instrumentation is used in conjunction with the biopsy forceps.

(b) The biopsy forceps uses a mechanism, such as a clevis pivot, which provides the jaws of the forceps with the greater force for closing the jaws than a hinged design, thus providing effective sample retrieval.

(c) By locating the cross hole appropriately in the clevis pivot, the diagnostic or procedural member can be centered between the two jaws.

(d) The diagnostic or procedural instrumentation can be incorporated into the biopsy forceps, eliminating the need for a second separate device.

(e) The design is simple and involves a minimum of components, which makes the device easy and inexpensive to manufacture.

Operation-FIGS. 2, 4

Referring to FIG. 4, the biopsy forceps is shown with jaws 22 in the closed position and the distal end of elongated diagnostic or procedural member 16 retracted to the proximal end of two cups 18. In this closed position, the distal portion of the biopsy forceps is advanced, usually through the working channel of an endoscope, to the tissue of which a sample is desired. This advancement is accomplished by manipulating the device from the proximal end of shaft 38.

Referring to FIG. 2, jaws 22 are then opened by manipulating the control mechanism (not shown) at the proximal end of shaft 38 in such a way that pull wires 28 are advanced distally through shaft 38 toward jaw assembly 8. Jaws 22 are prevented from moving distally by clevis pivot 10 which attaches jaws 22 to clevis 26. Thus, advancing pull wires 28 distally causes jaws 22 to rotate about clevis pivot 10. As a result, cups 18 are propelled away from each other, more so at the distal end than the proximal end. If desired, elongated diagnostic or procedural member 16 can be extended distally past the distal end of open jaws 22. In one embodiment of the invention, this may be done manually. In another embodiment, elongated diagnostic or procedural member 16 may be manipulated by the control mechanism (not shown), and possibly advanced automatically as jaws 22 are opened. The device is then advanced, by manipulation at the proximal end of shaft 38, so that jaws 22, and more particularly sharp rims 20, are pushed against the tissue surface.

Referring to FIG. 4, jaws 22 are then closed by manipulating the control mechanism (not shown) at the proximal end of shaft 38 in such a way that pull wires 28 are pulled proximally through shaft 38 away from jaw assembly 8. This causes jaws 22 to rotate about clevis pivot 10, resulting in cups 18 being propelled toward each other. The distal end of each pull wire 28, beyond the angled bends 34, fits into notch 36. If desired, elongated diagnostic or procedural member 16 can be retracted proximally toward the proximal end of cups 18. In one embodiment of the invention, this may be done manually. In another embodiment, elongated diagnostic or procedural member 16 may be manipulated by the control mechanism (not shown), and possibly retracted automatically as jaws 22 are closed. As the jaws close, sharp rims 20 of cups 18 cut into the tissue. As sharp rims 20 meet each other, the tissue sample becomes separated from the tissue and is held between the closed cups 18. The device can then be removed from the patient, maintaining enough force on the control mechanism, and thus pull wires 28, to keep jaws 22 closed in order to retain the tissue sample in cups 18. The jaw assembly 8 has a diameter less than four millimeters in the closed position.

Summary, Ramifications, and Scope

Accordingly, the reader will see that the biopsy forceps of this invention provides a device which uses a clevis pivot and incorporates a passageway through the shaft and jaw assembly. This biopsy forceps allows a second device, such as a diagnostic or procedural member, to be passed through the passageway. This makes possible the simultaneous use of two devices through an endoscope having only one working channel. Furthermore, this biopsy forceps has the additional advantages in that the clevis pivot design allows the jaws to be closed with a significant amount of force, providing effective sample retrieval;

the second device can be incorporated into the biopsy forceps, eliminating the need for two separate devices;

the diagnostic or procedural member can be centered between the two jaws; and the simple design makes it easy and inexpensive to manufacture.

Although the description above contains many specificities, these should not be construed as limiting the scope of the invention, but as merely providing illustrations of some of the presently preferred embodiments of this invention. For example, the elongated member may be a guide wire over which the biopsy forceps could be passed, as in vascular applications; the elongated member may be a diagnostic device which could, for example, verify the presence and size of a biopsy sample the elongated member may be a catheter; the device may be a medical forceps used for purposes other than obtaining a biopsy sample, such as grasping a foreign object; one of the jaws could be fixed in place, with only one jaw rotating about the clevis pivot; a single pull wire could be used; the rims of the jaws may be serrated the clevis pivot pin may be a threaded screw, etc.

Thus the scope of the invention should be determined by the appended claims and their legal equivalents, rather than by the examples given.

I claim:

1. A medical forceps jaw assembly comprising:
    a clevis having a pivot; pin
    a first jaw pivotally attached to said clevis by said clevis pivot pin, said first jaw having a limited rotation around said clevis pivot pin;
    a second jaw which opposes said first jaw;
    an opening through said clevis pivot pin said opening allows passage substantially along the center line of said jaw assembly;
    a drive member which is used to actuate at least one of said jaws, said drive member is capable of movement between a first proximal position and a second distal position which effects opening or closing between said jaws;
    an elongated member for diagnostic or procedural purposes with a center line substantially parallel to the center line of said jaw assembly, said elongated member passes through said opening in said clevis pivot pin whereby incorporation of said elongated member into said jaw assembly allows an additional diagnostic or procedural function to be performed by said medical forceps.

2. The medical forceps jaw assembly of claim 1 wherein each said jaw has a cup with a sharp rim for taking biopsy samples.

3. The medical forceps jaw assembly of claim 1 wherein each said jaw is a gripper.

4. The medical forceps jaw assembly of claim 1 wherein said drive member is a pair of pull wires, each of which has at least one angled bend at the distal end for engagement with said jaws.

5. The medical forceps jaw assembly of claim 1 wherein said clevis pivot pin is circular.

6. The medical forceps jaw assembly of claim 1 wherein said clevis pivot pin has a threaded portion.

7. The medical forceps jaw assembly of claim 1 wherein said elongated member is a guidewire.

8. The medical forceps jaw assembly of claim 1 wherein said elongated member is a catheter.

9. The medical forceps jaw assembly of claim 1 wherein said elongated member is a diagnostic probe.

10. The medical forceps jaw assembly of claim 1 wherein said jaw assembly has a diameter less than four millimeters in the closed position.

11. A medical forceps jaw assembly comprising:
    opposed jaws, said jaws each having a distal and a proximal end;
    an actuation means engaged at the proximal portion of at least one of said jaws to effect opening and closing movement at the distal portion of said jaws;
    a clevis including a pivot pin having a cross hole approximately parallel to the center line of said jaw assembly, at least one of said jaws pivotally attached to said clevis by said pivot pin;
    a passageway extending between the proximal portion of said jaws and through said clevis pivot pin, cross hole, whereby said passageway allows incorporation of an elongated member for diagnostic or procedural purposes.

12. The medical forceps jaw assembly of claim 11 wherein each said jaw has a cup with a sharp rim for taking biopsy samples.

13. The medical forceps jaw assembly of claim 11 wherein each said jaw is a gripper.

14. The medical forceps jaw assembly of claim 11 wherein said actuation means is a pair of pull wires, each of which has at least one angled bend at the distal end for engagement with said jaws.

15. The medical forceps jaw assembly of claim 11 wherein said clevis pivot pin is circular.

16. The medical forceps jaw assembly of claim 11 wherein said clevis pivot pin has a threaded portion.

17. The medical forceps jaw assembly of claim 11 further including a guidewire within said passageway.

18. The medical forceps jaw assembly of claim 11 further including a catheter within said passageway.

19. The medical forceps jaw assembly of claim 11 further including a diagnostic probe within said passageway.

20. The medical forceps jaw assembly of claim 11 wherein said jaw assembly has a diameter of less than four millimeters in the closed position.

* * * * *